United States Patent [19]

Hirosaki et al.

[11] 4,059,695

[45] Nov. 22, 1977

[54] METHOD FOR MANUFACTURING A TONIC COMPOSITION FOR MAN AND OTHER ANIMALS

[75] Inventors: Kanari Hirosaki; Shin Hirosaki, both of Miyazaki, Japan

[73] Assignee: Kanari Hirosaki, Japan

[21] Appl. No.: 658,813

[22] Filed: Feb. 17, 1976

Related U.S. Application Data

[63] Continuation-in-part of Ser. No. 481,235, June 20, 1974, abandoned.

[30] Foreign Application Priority Data

Feb. 14, 1974 Japan .................................. 49-017112

[51] Int. Cl.² .............................................. A61K 31/78
[52] U.S. Cl. .................................................... 424/195
[58] Field of Search .......................................... 424/195

[56] References Cited

U.S. PATENT DOCUMENTS

| 316,932 | 5/1885 | Baker | 424/195 |
| 446,058 | 2/1891 | Corey | 424/195 |

OTHER PUBLICATIONS

The Dispensatory of U.S.A., 24th Ed., (1947), pp. 10, 11, 943, 944 & 1621.

*Primary Examiner*—Stanley J. Friedman
*Attorney, Agent, or Firm*—Stevens, Davis, Miller & Mosher

[57] ABSTRACT

This invention relates to a method for a manufacture of a tonic composition for man and other animals, which method comprises dissolving effective components extracted from comfrey leaves and leaves of one or more plants by refined wood vinegar and refining the solution, wherein the extracted component and the refined wood vinegar have synergistic effects for activating bodies of man and other animals.

26 Claims, 6 Drawing Figures

METHOD FOR MANUFACTURING A TONIC COMPOSITION FOR MAN AND OTHER ANIMALS

BACKGROUND OF THE INVENTION

This application is a continuation-in-part of Ser. No. 481,235 filed on June 20, 1974 for "A TONIC COMPOSITION FOR MAN AND OTHER ANIMALS AND A METHOD FOR THE MANUFACTURE THEREOF", now abandoned.

It has heretofore been known to use wood vinegar as a smoking agent for fish meat and to employ it as a soil sterilizer and fungicide, as a repellent against nematodes inhabiting soil, as a deodorant for pigsties and henhouses, and as a preparation for cleaning and deodorizing rivers. Wood vinegar is a liquid composed of around 200 different organic compounds including about 3% acetic acid, about 1% other organic acids, a little less than 1% methanol and traces of aldehydes, ketones and phenols. Since these are invariably produced by the thermal decomposition of wood, wood vinegar is recognized not to possess any violent toxicity. Among the organic compounds present therein, however, formaldehyde, methanol, benzpyrene and benzanthracene are recognized to be harmful when injested by living creatures. Particularly, benzpyrene and benzanthracene are regarded as carcinogenic substances. It is, therefore, recognized to be harmful and improper for wood vinegar to be admixed in its unmodified form with food and consumed by man and other animals.

The present inventors studied wood vinegar in looking for a tonic composition which is free from these drawbacks and yet usable for man as well as for other animals. They discovered that refined wood vinegar is obtained by allowing wood vinegar obtained by a conventional method, or preferably wood vinegar of the type produced from nine or more different types of trees as raw materials, to age by standing at rest for several years then refining the aged wood vinegar by thoroughly removing soluble tars unsuitable for ingestion by living creatures. Further, by adding leaves of a plant to the refined wood vinegar and allowing the leaves to be permeated by the wood vinegar they have obtained a product which, when added to feed and taken by domestic animals, encourages the animals to take the feed, promotes their health and growth, deodorizes their excrements as well as their bodies, improves the hygiene of their environments and consequently prevents otherwise possible public nuisance. Also, when taken by man, the product serves to promote his health. This knowledge has served as a basis for the present invention.

SUMMARY OF THE INVENTION

The present invention provides a tonic composition in liquid form for man and other animals made up essentially of refined wood vinegar containing plant leaf components.

The present invention further provides a tonic composition for man and other animals in a form of powder or granular solid in which said liquid tonic is absorbed on a soft amorphous carbon powder.

The present invention also provides a method for the manufacture of a tonic composition for man and other animals, comprising adding leaves of one or more plants to refined wood vinegar to ferment or permeate the leaves in refined wood vinegar, thereafter filtering the leaves' residue and refining the filtrate. The refined filtrate may be adsorbed on a soft amorphous carbon powder, to provide a tonic composition in solid form.

DETAILED DESCRIPTION OF THE INVENTION

Figure 1:
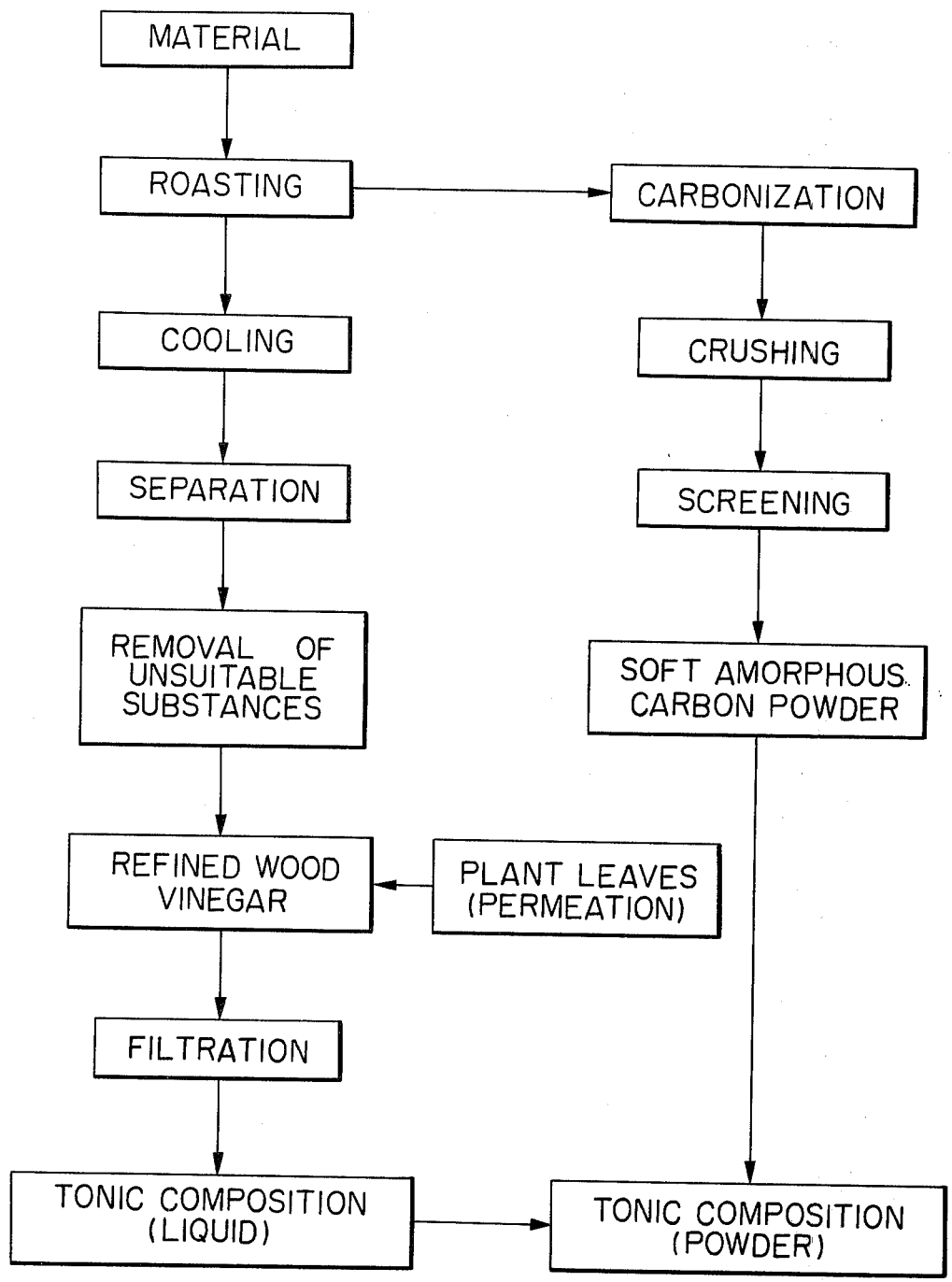
FIG. 1 illustrates a manufacturing process of the present invention.

The refined wood vinegar to be used for this invention is produced as illustrated in FIG. 1 by refining wood vinegar obtained by a conventional method or by chipping trees (enumerated herein below) or barks of such trees, placing the chips in a metallic retort or a kiln built with stones or bricks, roasting the chips therein in the absence of air to obtain volatile substances produced by the decomposition of water and wood compounds contained in the chips, liquefying the volatile substances through a condenser, allowing the liquefaction product to stand at rest, withdrawing the wood vinegar occurring as a supernatant, allowing this wood vinegar to stand at rest in a storage tank for several years, more preferably over five years, and subjecting to washing and distillation with benzene the supernatant or the upper of the two phases into which the wood vinegar is separated after the standing. The soluble tars which have survived the first washing and distillation with benzene are repeatedly subjected to a procedure of separation comprising the steps of distillation, agitation and standing until complete removal is obtained. Consequently, there is obtained refined wood vinegar which is completely free from benzpyrene, benzanthracene and other substances unsuitable for ingestion by living creatures. When the crude wood vinegar is left to stand at rest for several years, or preferably for more than 5 years, it matures and soluble tars partially dissolved therein sediment to a lower phase, so that highly refined wood vinegar is produced efficiently. Since the tonic composition according to this invention is intended for use by man and domestic animals, the removal of substances unsuitable for ingestion by living creatures must be effected to a thorough extent.

The leaves referred to in the present invention are preferably comfrey (*Symphytum officinale*) leaves or a mixture of leaves the majority of which are comfrey leaves and including leaves of bamboo (bambusa), garden radish (*Raphnus satious*) and matrimony vine (*Lycium vulgare*). Sasa albomarginata can be further added therein. They may be added to the refined wood vinegar from which substances unsuitable for ingestion by living creatures have been thoroughly removed as mentioned above and allowed to stand at rest for three to five months. Alternatively, the comfrey leaves of the mixed leaves are completely replaced at intervals of one to three months, preferably of two months, over a period longer than one year. Consequently, the leaves are sufficiently permeated in the refined wood vinegar. Thereafter, the resultant mixture is filtered and the filtrate is distilled to give rise to a liquid tonic for man and other animals.

Refined wood vinegar is used for the reason that wood vinegar, by incorporating various organic compounds, metallic elements and other substances, manifests tonic effects in man and other animals. The reason for the addition of comfrey leaves or a mixture containing a majority of comfrey leaves and supplementally incorporating leaves of bamboo, garden radish and matrimony vine to this refined wood vinegar is that special emphasis is placed on germanium, allantoin, vitamin $B_{12}$ and vitamin B which occur particularly in comfrey leaves. The leaves of bamboo, garden radish and matrimony vine are supplementally incorporated for the reason that components other than those present in the comfrey leaves such as, for example, vitamin K, vitamin B and vitamin C contained in the bamboo leaves, potassium, calcium, vitamin C and various vitamins in the garden radish leaves and betaine and rutin in the matrimony vine leaves function synergistically with the refined wood vinegar to give tonic effects for man and other animals.

For the production of wood vinegar according to this invention, although trees which are generally used for the production of wood vinegar are usable, it is desirable to use deciduous trees or a mixture of deciduous and coniferous trees. It is especially advantageous to use the nine essential species of trees consisting of (1) Akagashi (*Quercus acuta* Thunbs.), (2) Shirogashi (*Quercus myrsinaefolia* Blume), (3) Arakashi (*Quercus glauca* Thunb.), (4), Ichiigashi (*Quercus gilva* Blume of genus *Quercus L.*); (5) Kojii (*Shiia cuspidata* Makino) and (6) Itajii (Shiia Sieboldini Makino) of genus Castanopsis Spach., (7) Shiratabu (*Litsea glauca* Sieb.), (8) Benitabu (Machilus Thunbergii Sieb.) and (9) Camphore tree (Cinnamomum Camphora Sieb.) of Family Lauracae, and thereto to add at least one of the optional species of trees including wild cherry tree (*Prunus donarium* Sieb. var. spontanea Makino) and other species of the Rose Family (Rosaceae); species such as Yusu (*Distylum racemosum* Sieb. et Zucc.) of the Witch-hazel Family (Hamamelidaceae); Japanese oak (alias petit oak) (*Quercus serrata* Tumb.) and other species of the genus Quercus L., Beech Family (Fagaceae); such species as Kunugi (*Quercus acutissima* Carruth) and Beech (*Fagus crenate* Blume) of the genera *Quercus L* and *Fabus L.*, Beech Family (Fagaceae); such species as *Carpinums laxiflora* Blume of the genus *Carpinus L.*, Birch Family (Betulaceae); such species as Mizume (*Betula grossa* sieb. et Zucc.) of the genus *Bebula L.*, Birch Family (Betulaceae); maple tree (*Acer palmatum* Thunb.) and other species of the Acer L. Maple Family (Aceraceae); zelkova tree (zelkova serrata Makino) and other species of the genus Zelkova Spach., Elm Family (Ulmaceae); myrica (Myrica Rubra Sieb. et Zucc) and other species of the Myrica Family (Myricaceae); scaber (Euphorbia Pekinensis Rupr. var. Japonesis Makino) and other species of the Spurge Family (Euphorbiaeceae); such species as Harigiri (Kalophanax septemlobus Koidz.) of the Ginseg Family (Araliaceae); swmp nut (*Pterocarya rhoifolia* Sieb. et Zucc.) walnut (*Juglans mandshurica* Maxim. var. Sieboldiana Makino) and other species of the Walnut Family (Juglandaceae); Camellia (*Camellia japonica L.*) and other species including Himeshara (*Stewartia mondadelpha* Sieb. et Zucc.) of the Tea Family (Theaceae); oak (*Quercus dentata* Thunb.) and other species of the genus *Quercus L.*, Beech Family (Fagaceae); wax tree (*Rhus succedanea L.*) and other species of the Sumac Family (Anacardiacea); Japanese cedar (*Cryptomeria japonica* D. Don) and other species of the genus *Cryptomeria* D. Don, Pine Family (Pinaceae); ground-cypress (*Chamaecyparis pbtusa* Endl.) and other species of the genus Chamaecyparis Spach., Pine Family (Pinaceae); pine tree (Pinus Thunbergii Part.) and other species of the genus *Pinus L.*, Pine Family (Pinaceae); hemlock spruce (Tsuga Sieboldii Carr.) and other species of the genus Tsuga Carr, Pine Family (Pinanceae); and white fir (*Abies firma* Sieb. et Zucc) of the genus Abies Mill., Pike Family (Pinaceae). (See, for example, pages 85, 88, 90–92, 192–194, 249, 393 and 431 of Makino's New Illustrated Flora of Japan, as a reference for identifying such species and their technical names.)

The desirability of the combined use of the trees described above has been demonstrated by the inventors' experiment which has led to the following conclusion: When the refined wood vinegar obtained by using the aforementioned nine species of trees in conjunction with other species is employed, a synergistic effect is produced when comfrey leaves or a mixture containing a majority of comfrey leaves and supplementally incorporating leaves of bamboo, garden radish and matrimony vine are added thereto and allowed to be permeated by the refined wood vinegar. The tonic composition consequently produced, it has been demonstrated, far excells that which is obtained with a wood vinegar produced by using a smaller number of trees.

In preparing the comfrey leaves or a mixture containing a majority of comfrey leaves and supplementally incorporating leaves of bamboo, garden radish and matrimony vine, the amount of leaves to be added to the refined wood vinegar falls, in practice, in a range from about 0.1 to 10 parts by weight based on 100 parts by weight of the refined wood vinegar. It has been experimentally confirmed that if the amount is smaller than the lower limit, 0.1 part by weight, then the effect of the product fails to reach the desired level, and if the amount exceeds the upper limit 10 parts by weight, the leaves are wasted without bringing about any extra effect. It is preferable to use the comfrey leaves independently. If a mixture of leaves is used, the comfrey leaves preferably comprise as a large proportion as possible, for example not less than 90% by weight, to obtain the cellulase type crude enzyme. In the comfrey leaves, vitamine $B_{12}$, vitamine B, allantoin, germanium, etc. are contained as active components. These components are permeated and dissolved by the refined wood vinegar and, therefore, produce useful functions on man and other animals. When a mixture of leaves is used, the proportions by weight of comfrey leaves and the leaves of bamboo, garden radish and matrimony vine are in the ranges of about 85–99% comfrey, about 0–15% bamboo, about 0–15% garden radish and about 0–15% matrimony vine. Desirably, the combined amount of the leaves of bamboo, garden radish and matrimony vine to be added to the comfrey leaves is such as to give a ratio by weight of about 1 to 100 of the comfrey leaves.

It is also possible to produce a granular or powdery solid tonic composition as illustrated in FIG. 1 by adding to the refined wood vinegar a soft amorphous carbon powder obtained for example by roasting bark and chips of deciduous trees or those of a mixture of about 90–99% of deciduous trees by weight and about 10–1% of coniferous trees by weight at about 350° C for about 20 to 500 hours, preferably for about 200 to 300 hours, crushing and acreening the obtained carbide. It is particularly desirable that the adsorption of the refined wood vinegar with carbon powder is carried out several times separated by drying. Although the most suitable temperature for the roasting is 350° C, the range of about 250° to 450° C suffices for the purpose. A desirable amount of soft amorphous carbon powder to be admixed is about two to six times, preferably about three to four times, the weight of the refined wood vinegar. When the tonic composition in the form of a granular or powdery solid is ingested into the system of man and other animals, the soft amorphous carbon powder serves to adsorb the gases of indole and skatole types generated in consequence of the hydrolysis of starches in the goods taken by man and other animals, and also functions to control the environment of microorganisms within the systems. The tonic composition in the form of a granular or powdery solid has various advantages such as being economical, facilitating its preservation and management, transportation and handling, and being easily added or admixed into animal feed. Incidentally, the deciduous trees or a mixture containing a major fraction of deciduous trees and a minor fraction of coniferous trees, which serve as the raw material for the soft amorphous carbon powder, are identical with those which are employed for the preparation of wood vinegar. The soft amorphous carbon powder obtained as described above is preferably finely divided to a particle diameter of not less than 300 mesh (ASTM E-11-61) for use by man. When it is intended for use by other animals, it is preferably divided into a particle diameter of the order of 100-300 mesh (ASTM E-11-61) to facilitate admixture with animal feed. Zeonerite can be used instead of the soft amorphous carbon powder without causing any change in the effects.

The tonic composition of the present invention as described above was found to have the following main properties and contents:

| 1. Properties | |
|---|---|
| Specific gravity | 0.98 to 1.01 |
| pH | 3.5 to 4.18 |
| Acidity (as acetic acid) | 0.80 to 1.30% by weight |
| 2. Composition | |
| A) Organic acids | |
| Acetic acid | 0.46 to 0.47% by weight |
| Propionic acid | 0.30 to 0.31% by weight |
| Valeric acid | 0.14 to 0.15% by weight |
| Other organic acids | 0.30 to 0.29% by weight |
| B) Weakly acidic compounds (about 0.21%) Guaiacol, ethyl guaiacol, paracresol, etc. | |
| C) Neutral components (0.02% by weight) Ketones - Acetone, methylethyl ketone, methylpropyl ketone and methylisopropyl ketone Aldehydes - Acetaldehyde, isobutyl aldehyde, propionaldehyde, acryl aldehyde, butyl aldehyde, valeraldehyde and isovaleraldehyde, etc. | |
| D) Others (about 0.05% by weight) Rare elements such as allantoin, vitamin B group, pure protein and germanium, etc. | |

From the foregoing analysis, it is seen that the tonic composition is a liquid with a weakly acidic odor which contains numerous rare components other than organic components and exhibits catalytic action and pharmacological activities on living systems.

The tonic composition according to the present invention was further subjected to luminous spectroscopic analysis for determination of useful nutrient components for living organisms. The results of this analysis are shown in Table 1.

Table 1

| Element | Wavelength (in A) | Strength of Analytical line | Element | Wavelength (in A) | Strength of Analytical line |
|---|---|---|---|---|---|
| | 3082 | + | | 2516 | + |

Table 1-continued

| Element | Wavelength (in A) | Strength of Analytical line | Element | Wavelength (in A) | Strength of Analytical line |
|---|---|---|---|---|---|
| Al | 3092 | ++ | Si | 2524 | + |
| | 2816 | + | | 2881 | + |
| | 3158 | ++ | | 3302 | + |
| Ca | 3179 | ++ | Na | | |
| | 4226 | +++ | | 3303 | + |
| | 4254 | + | | 3009 | + |
| Cr | 4274 | + | Sn | 3175 | + |
| | 4289 | +++ | | 3262 | ++ |
| | 3247 | + | | 2743 | ++ |
| Cu | | | Fe | 2749 | ++ |
| | 3273 | + | | 2755 | ++ |
| | 2795 | ++ | | 2794 | + |
| Mg | 2802 | ++ | Mn | 2798 | + |
| | 2852 | + | | 2801 | + |

In the preceding table, the strength of the analytical line was rated by a scale, in which the symbols denote the following:

− Absence of discernible analytical line
± Unclear analytical line
+ Analytical line discernible
++ Analytical line clearly observed
+++ Analytical line strongly observed Analytical apparatus: EPART type emission spectroanalysis analyzer made by Shimadzu Seisakusho Emission conditions: Electrode gap 3 mm, slit width 15 μ, excitation source DC Arc., current 5A, electrode emission graphite made by Hitachi Seisakusho, regular 5 mm Diam.

Wavelength range (measurement): 2000 to 4500 A, exposure time 45 sec.

The foregoing results indicate that the principal components of the tonic according to this invention are weakly acidic, account for 60% by weight of the dissolved components and are invariably utilized as substances belonging to the class of carbolic acids. Therefore, these components exhibit strong disinfecting, anticepticizing and deodorizing activities. Of the components, those of the pyrogallol type function most effectively as deodorants and also serve as insectifuges capable of paralyzing parasites (specifically tapeworms and roundworms) inhaviting in the living organisms. Of the secondary components, the neutral components account for only about 20% by weight. They are invariably carbonyl compounds (aldehydes and ketones). Among the aldehydes present, formaldehyde is contained at a concentration of only 6.0 ppm.

The detoxication action of the tonic composition prepared according to the present invention is hereinafter disclosed with reference to the changes in liver function of rats which were dosed by oral administration Liver function examination often has been carried out to examine whether there is any liver trouble caused by a substance given.

Using Alkaline Phospha K-Test wako and S. TA-Test wako (serum transaninase) of Wako K.K., GOT (glutamic oxaloacetic transaminase), GPT (glutamic pyruvic transaminase) and alkali phosphatase were measured by giving the tonic composition to rats. The tonic composition of 1 ml/200g was given to rats for 14 days. This amount is 75 times the amount usually given to man. The test results are shown in the following table.

Table 2

| | Control group | | | | Test group | | |
|---|---|---|---|---|---|---|---|
| No. | GPT | GOT | Alkali phosphatase | No. | GPT | GOT | Alkali phosphatase |
| 1 | 41.0 | 160.0 | 40.0 | 1 | 31.0 | 102.0 | 17.0 |
| 2 | 44.0 | 150.5 | 120.0 | 2 | 29.0 | 102.0 | 12.0 |
| 3 | 33.0 | 132.0 | 36.0 | 3 | 40.0 | 133.0 | 105.0 |
| 4 | 41.0 | 160.0 | 25.0 | 4 | 40.0 | 195.0 | 25.0 |
| 5 | 31.0 | 160.0 | 20.0 | 5 | 25.0 | 67.0 | 30.0 |
| Average | 38.0 Karmen unit | 152.5 Karmen unit | 26.6 K-A unit | Average | 33.0 Karmen unit | 119.8 Karmen unit | 37.8 K-A unit |

Judging from the above, the tonic composition of the present invention seems not to cause any liver trouble. And considering the amount of the composition given to rats, this composition seems not to have toxicity.

The tonic composition of the present invention, upon ingestion, manifests tonic properties. In particular it may be of assistance in the following circumstances: (1) alleviating constipation and abnormal corpulence, (2) assisting the gastrointestinal organs in their digestive and assimilative functions, (3) deodorizing the body, (4) assisting in the treatment of diabetes, (5) mitigating arthritis, and (6) invigorating the system. The tonic composition of the present invention is harmless to man and other animals and involves no secondary effects.

As for the manner of use, the recommended dosage for an adult man is about 3 to 4 cc of the tonic composition diluted with water to about 50 to 100 times the original volume, taken on two or three separate occasions per day. The dosage for an infant may be less than one third of that for the adult.

Biochemical blood tests and liver function tests were carried out after the oral administration of the present tonic composition produced by the method of the present invention. The test results are shown in the following table. The oral administration of the tonic composition for 1.5 months and 2 months respectively was observed to normalize transaminase of GOT and GPT. Also, there was observed a tendency to normalize blood sugar and blood pressure at the time with an empty stomach. And the test using a neurometer was also carried out to observe the efficacy of the tonic composition of the present invention. The results are also shown in Tables 3 and 4.

Table 3

| | | | 33 year old male Decline of liver function | | | | | | 35 year old male hepatitis | | | | |
|---|---|---|---|---|---|---|---|---|---|---|---|---|---|
| BIOCHEMICAL BLOOD TEST | | | before use | 72nd day | 119th day | 147th day | 157th day | 298th day | before use | 36th day | 59th day | 93rd day | 128th day | 160th day |
| | | Number of red corpuscle | 491 | 476 | 490 | 390 | 506 | 526 | 412 | 461 | 412 | 480 | 461 | 449 |
| | | Number of leucocytes | 5,600 | 6,000 | 5,300 | 4,800 | 4,600 | 6,100 | 4,500 | 4,600 | 3,900 | 4,600 | 4,200 | 5,600 |
| | | Hemoglobin (g/dl) | 14.7 | 14.6 | 15.0 | 12.3 | 14.8 | 15.1 | 13.4 | 13.2 | 11.7 | 14.2 | 13.7 | 13.2 |
| | | Hematocrit (%) | 43.2 | 42.6 | 44.6 | 35.8 | 42.5 | 43.4 | 40.8 | 40.4 | 35.4 | 43.5 | 41.4 | 36.1 |
| | | Mean corpuscular volume ($\mu^3$) | 88 | 89 | 91 | 87 | 85 | 83 | 100 | 88 | 86 | 90 | 89 | 84 |
| | | Mean corpuscular hemoglobin ($\mu\mu g$) | 29.9 | 30.6 | 30.5 | 30.4 | 29.3 | 28.5 | 32.7 | 28.5 | 28.3 | 29.8 | 29.6 | 29.2 |
| | | Mean corpuscular hemoglobin concentration (%) | 34.3 | 34.1 | 34.0 | 34.6 | 34.9 | 34.7 | 33.2 | 32.8 | 30.6 | 32.7 | 32.9 | 34.6 |
| | | Stab form leukocytes (%) | | 7 | | 3 | | 2 | 3 | 5 | 5 | 6 | 6 | 5 |
| hemogram | | Segmented leukocytes (%) | | 58 | | 55 | | 42 | 35 | 43 | 46 | 39 | 46 | 46 |
| | | Lymphocytes (%) | | 31 | | 32 | | 50 | 58 | 48 | 44 | 52 | 44 | 44 |
| | | Monocytes (%) | | 1 | | 2 | | 2 | 2 | 4 | 2 | 2 | 2 | 2 |
| | | Eosinophilecytes (%) | | 3 | | 8 | | 3 | 1 | 0 | 2 | 1 | 1 | 2 |
| | | Basophiliecytes (%) | | 0 | | 0 | | 1 | 1 | 0 | 1 | 0 | 1 | 1 |
| LIVER FUNCTION TEST | | | | | | | | | | | | | | |
| | | Total bilirubin (mg/dl) | 0.9 | 0.7 | 0.6 | 0.9 | 0.7 | 0.5 | 1.2 | 1.2 | 1.3 | 0.8 | 1.6 | 1.8 |
| | | Thymol TTT (U) | 8 | 6 | 0.9 | 0.7 | 0.8 | 0.3 | 4 | 4 | 0.4 | 2 | 0.3 | 0.2 |
| | | ALP (U) | 12.3 | 12 | 7.7 | 5.8 | | | | | | | | |
| | | GOT (U) | 60 | 52 | 104 | 14 | | | | | | | | |
| | | GPT (U) | 45 | 40 | 69 | 6 | | | | | | | | |
| | | LDH (U) | 250 | 180 | 380 | 350 | | | | | | | | |
| | | ChE ($\Delta$ pH) | 2.0 | 1.2 | 1.5 | 1.4 | | | | | | | | |
| | | Total cholesterol (mg/dl) | 235 | 220 | 190 | 200 | | | | | | | | |

Table 3-continued

| | | | | | | | |
|---|---|---|---|---|---|---|---|
| 6.8 | 8.8 | 13 | 4.9 | 4.3 | 4.8 | 4.0 | 4.5 |
| 22 | 15 | 68 | 35 | 18 | 26 | 15 | 16 |
| 13 | 6 | 45 | 25 | 7 | 15 | 8 | 8 |
| 310 | 325 | 490 | 360 | 320 | 300 | 280 | 320 |
| 0.8 | 1.2 | 1.1 | 1.0 | 1.0 | 0.8 | 0.9 | 1.0 |
| 180 | 185 | 390 | 270 | 230 | 180 | 194 | 160 |

Normal value

♂ $4.10 - 5.30 \times 10^4$ ♀ $3.80 - 4.80 \times 10^4$
$4.0 - 8.5 \times 10^3$
♂ 14 – 18, ♀ 12 – 16
♂ 40 – 55, ♀ 37 – 47
80 – 99
27 – 31
32 – 36
3 – 6
45 – 55
25 – 40
44 –6
1 – 3
0 – 1
0.4 – 0.8
less than 4
4 – 12
10 – 40
8 – 30
50 – 400
0.8 – 1.1
120 – 250

| | | | | | | |
|---|---|---|---|---|---|---|
| Protein fraction | Alubumin (%) | | 64.1 | 59.7 | 65.8 | |
| | Globulin (%) | | 35.9 | 40.3 | 44.2 | |
| | $\alpha_1$ (%) | | 3.1 | 4.8 | 4.7 | |
| | $\alpha_2$ (%) | | 7.0 | 12.7 | 8.2 | |
| | $\beta$ (%) | | 11.0 | 7.9 | 6.6 | |
| | $\gamma$ (%) | | 14.5 | 14.7 | 14.5 | |
| | A/G | | 1.80 | 1.48 | 1.93 | |
| Neurometry | Maximum | | 50 | 30 | 30 | 20 |
| | Minimum | | 15 | 10 | 10 | 5 |
| | Average | | 33.7 | 19.4 | 19.4 | 10.6 |
| | + | | 3 | 2 | 2 | 1 |
| | 0 | | 19 | 22 | 22 | 23 |
| | − | | 2 | 0 | 0 | 0 |
| | Stability of autonomic nerve | | | | | |

| | | | | | | | |
|---|---|---|---|---|---|---|---|
| 61.0 | 58.3 | 63.5 | 64.3 | | 64.4 | 62.1 | 62.9 |
| 39 | 41.7 | 36.5 | 35.7 | | 35.6 | 37.9 | 37.1 |
| 4.2 | 4.6 | 3.3 | 2.9 | | 3.2 | 3.6 | 5.1 |
| 9.3 | 9.6 | 11.3 | 9.0 | | 9.6 | 11.1 | 9.7 |
| 10.3 | 7.5 | 11.7 | 9.4 | | 7.6 | 9.2 | 8.4 |
| 15.0 | 19.8 | 10.0 | 14.1 | | 15.0 | 13.8 | 13.7 |
| 1.57 | 1.40 | 1.70 | 1.80 | | 1.81 | 16.4 | 1.70 |
| 20 | 10 | 140 | 80 | 30 | 20 | 20 | 20 |
| 5 | 5 | 0 | 10 | 10 | 5 | 5 | 10 |
| 12.1 | 10.5 | 31.6 | 37.5 | 17.5 | 10.8 | 10.6 | 22.1 |
| 2 | 0 | 6 | 5 | 3 | 0 | 0 | 0 |
| 21 | 24 | 8 | 15 | 21 | 23 | 24 | 24 |
| 1 | 0 | 10 | 4 | 0 | 1 | 0 | 0 |
| | | 33 | 62 | 87 | 96 | 100 | 100 |

56.9 – 70.5
43.1 – 29.5
2.0 – 4.8
6.1 – 10.5
6.7 – 10.3
9.7 – 22.1
1.2 – 2.4
20 – 24

Table 4

| BIOCHEMICAL BLOOD TEST | | 35 year old male acute hepatitis | | 76 year old female hyperpiesia & liver function depression | |
|---|---|---|---|---|---|
| | | before use | after 1 month | before use | after month |
| | Number of red corpuscle | $449 \times 10^4$ | $461 \times 10^4$ | $438 \times 10^4$ | $437 \times 10^4$ |
| | Number of leucocytes | 4,500 | 4,600 | 4,500 | 4,500 |
| | Hemoglobin (g/dl) | 13.2 | 13.1 | 13.7 | 13.6 |
| | Hematocrit (%) | 39 | 40.4 | 40.6 | 40.9 |
| | Mean corpuscular volume ($\mu 3$) | 85 | 88 | 92 | 93 |
| | Mean corpuscular hemoglobin ($\mu\mu g$) | 29.5 | 28.5 | 31.3 | 31.3 |
| | Mean corpuscular hemoglobin concentration (%) | 34 | 32.8 | 33.9 | 33.4 |

Table 4-continued

| | | | | | |
|---|---|---|---|---|---|
| Hemogram | Stab form leukocytes (%) | 5 | 5 | 4 | 4 |
| | Segmented leukocytes (%) | 47 | 43 | 45 | 46 |
| | Lymphocytes (%) | 45 | 48 | 55 | 46 |
| | Monocytes (%) | 2 | 4 | 5 | 2 |
| | Eosinophilecytes (%) | 1 | 0 | 1 | 2 |
| | Basophiliecytes (%) | 0 | 0 | 0 | 0 |
| LIVER FUNCTION TEST | | | | | |
| | Total bilirubin (mg/dl) | 1.0 | 1.2 | 0.7 | 0.4 |
| | Thymol TTT (U) | 9 | 4 | 6 | 3 |
| | ALP (U) | 19.5 | 4.9 | 15.2 | 5.3 |
| | GOT (U) | 75 | 35 | 67 | 11 |
| | GPT (U) | 62 | 25 | 45 | 5 |
| | LDH (U) | 520 | 360 | 200 | 180 |
| | ChE (ΔpH) | 1.1 | 1.1 | 1.1 | 0.9 |
| | Total cholesterol (mg/dl) | 390 | 250 | 200 | 180 |

| 42 year old male diabetes | | 67 year old male hypertension | | Normal value |
|---|---|---|---|---|
| before use | 2 months later | before use | 1.5 months later | |
| 484 × 10⁴ | 509 × 10⁴ | 467 × 10⁴ | 437 × 10⁴ | ♂ (4.0–5.3) × 10⁴, ♀ (3.8–4.5) × 10⁴ |
| 5,200 | 7,900 | 8,600 | 5,400 | (4.0 – 4.5) × 10³ |
| 14.2 | 15.1 | 13.9 | 13.9 | ♂ 14 – 18, ♀ 12 – 16 |
| 41.9 | 45.3 | 43 | 42 | ♂ 40 – 55, ♀ 37 – 47 |
| 87 | 89 | 94 | 96 | 80 – 99 |
| 29.4 | 29.8 | 30.9 | 31.9 | 27 – 31 |
| 34.1 | 33.9 | 32.6 | 33.1 | 32 – 36 |
| 2 | 5 | 4 | 5 | 3 – 6 |
| 47 | 53 | 60 | 45 | 45 – 55 |
| 47 | 37 | 33 | 48 | 25 – 40 |
| 3 | 2 | 2 | 2 | 4 – 6 |
| 0 | 3 | 1 | 0 | 1 – 3 |
| 0 | 0 | 0 | 0 | 0 – 1 |
| 0.8 | 0.6 | 0.8 | 0.6 | 0.4 – 0.8 |
| 0.5 | 0.4 | 4 | 1.2 | less than 4 |
| 6.3 | 5.6 | 12.5 | 9.7 | 2.7 – 10 |
| 72 | 31 | 57 | 17 | 10 – 40 |
| 57 | 28 | 45 | 9 | 8 – 30 |
| 310 | 280 | 300 | 350 | 50 – 400 |
| 0.9 | 1.1 | 0.8 | 1.0 | 0.8 – 1.1 |
| 244 | 200 | 230 | 210 | 120 – 250 |

| | | | | | | |
|---|---|---|---|---|---|---|
| Protein fraction | Albumin (%) | | | 63.5 | 64.3 | 56.2 | 54.3 |
| | Globulin (%) | | | 36.5 | 35.7 | 43.8 | 41.1 |
| | α₁ (%) | | | 3.3 | 2.9 | 4.3 | 5.3 |
| | α₂ (%) | | | 11.3 | 9.0 | 11.1 | 10.6 |
| | β (%) | | | 11.7 | 9.4 | 16.7 | 14.9 |
| | γ (%) | | | 10.0 | 14.1 | 1.3 | 1.4 |
| | A/G | | | 1.7 | 1.8 | 1.3 | 1.4 |
| Others when hungry | Fixed quantity of blood sugar (mg/dl) | | | | | | |
| | Blood pressure (Max.) (mmHg) (Min.) | | | | | | |
| Neurometry | Maximum | | | 130 | 140 | 40 | 30 |
| | Minimum | | | 0 | 10 | 0 | 10 |
| | Average | | | 16.6 | 32.1 | 12.3 | 25.6 |
| | + | | | 3 | 3 | 7 | 1 |
| | 0 | | | 1 | 15 | 10 | 22 |
| | − | | | 20 | 6 | 7 | 1 |

| | | | | |
|---|---|---|---|---|
| 58.8 | 55.6 | 60.7 | 59.5 | 56.9 – 70.5 |
| 41.2 | 44.4 | 39.3 | 40.5 | 43.1 – 29.5 |
| 3.8 | 5.5 | 4.1 | 4.8 | 2.0 – 4.8 |
| 11.0 | 12.3 | 7.5 | 9.6 | 6.1 – 10.5 |
| 13.1 | 10.8 | 11.7 | 10.4 | 6.7 – 10.3 |
| 13.1 | 15.5 | 15.8 | 15.7 | 9.7 – 22.1 |
| 1.4 | 1.3 | 1.5 | 1.5 | 1.1 – 1.7 |
| 120 | 100 | | | less than 100 |
| 130 | 120 | 180 | 160 | 120 – 150 |
| 80 | 80 | 120 | 100 | 70 – 90 |
| 40 | 50 | 100 | 30 | 40 ± 10 |
| 0 | 5 | 0 | 10 | 20 ± 10 |
| 5.9 | 9 | 33.7 | 25.6 | 40 ± 10 |
| 3 | 1 | 8 | 1 | 0 – 2 |
| 11 | 21 | 4 | 22 | 20 – 24 |
| 10 | 2 | 12 | 1 | 0 – 2 |

Note:
By means of Neurometer, autonomic nerves can be examined, so that it can be known in a short period of time whether one is healthy, in poor health or ill.

Note:
TTT = Thymol turbidity test
ALP = Alkaline phosthatase
LDH = lactic dehydrogenase
ChE = Cholinesterase Health means the stable state of the automatic nervous system of the whole body. When one is ill, the degree of autonomic imbalance is strong.

Figure 2:
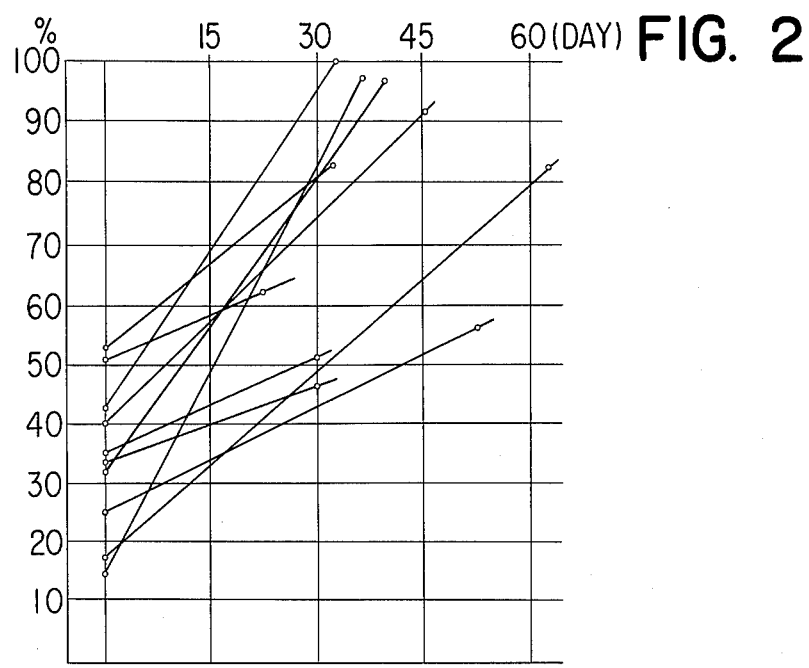
FIGS. 2 to 6 illustrate the efficacy of the tonic composition prepared by the present method.

FIG. 2 is a graph of data measured by neurometer, showing the improvement of the automatic nerve stability rate of a patient who took the tonic composition of the present invention. The stability rate is gradually approaches 100% from the average 50% as the days go by. In taking the tonic composition produced by the method of this invention, clinical efficacy, neurometry for the presence of an adverse reaction and close hematological examination are parts of experiment carried out along with various function tests.

Figure 3:
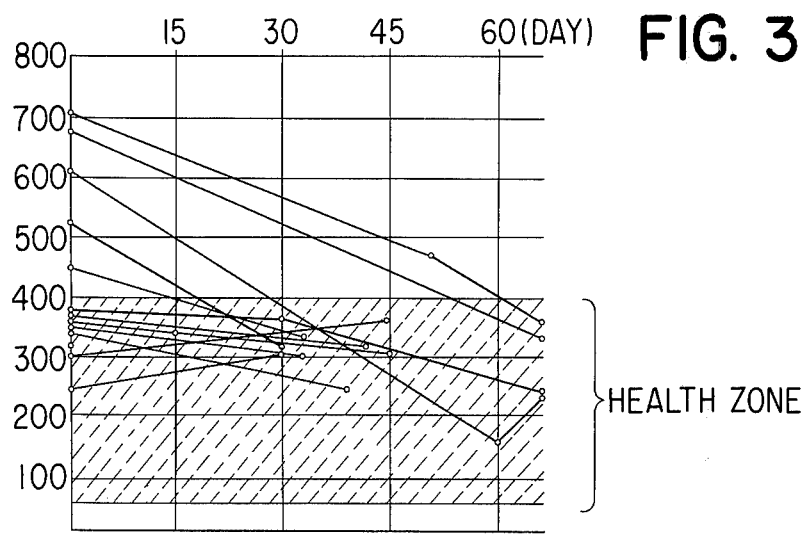

FIG. 3 shows the shifting of the serum enzyme activity value (liver function test LDH) by the administration of the tonic composition. This proves that the value is moving into the health zone as time goes by.

Figure 4:
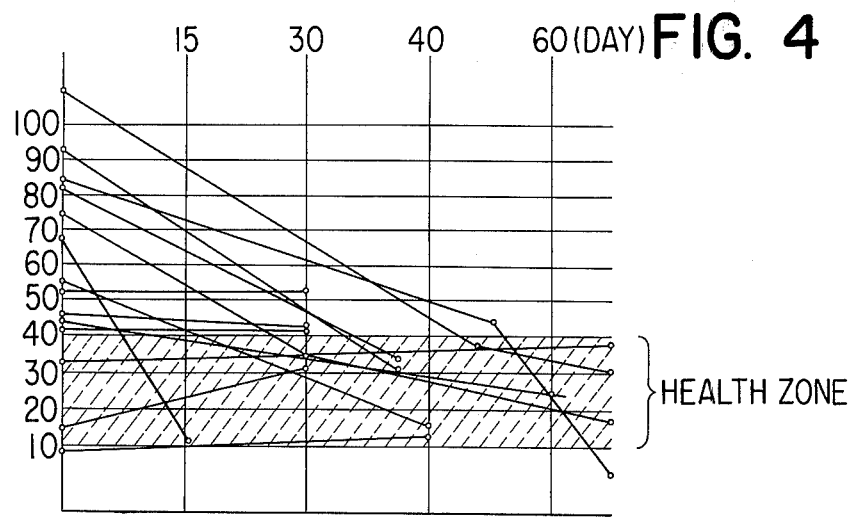

FIG. 4 shows also the result of liver function test GOT by the administration of the tonic composition and proves that the activity value is moving into the health zone as time goes by.

Figure 5:
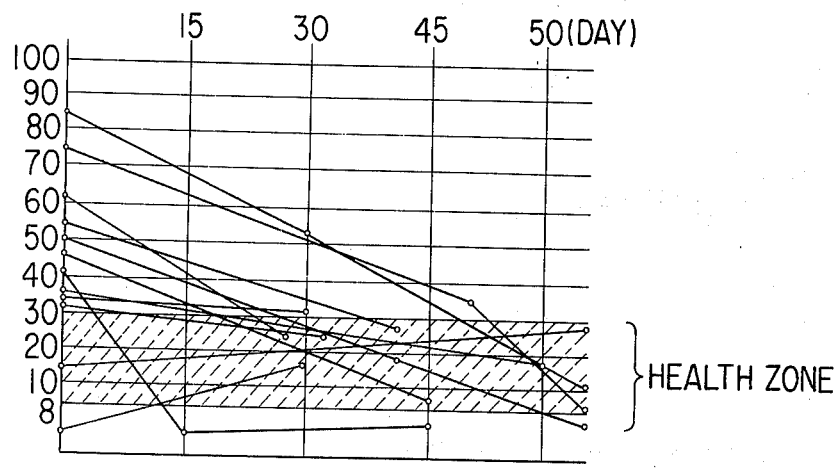

FIG. 5 shows the result of liver function test GPT by the administration of the tonic composition and proves that the value is moving into the health zone as time goes by.

Figure 6:
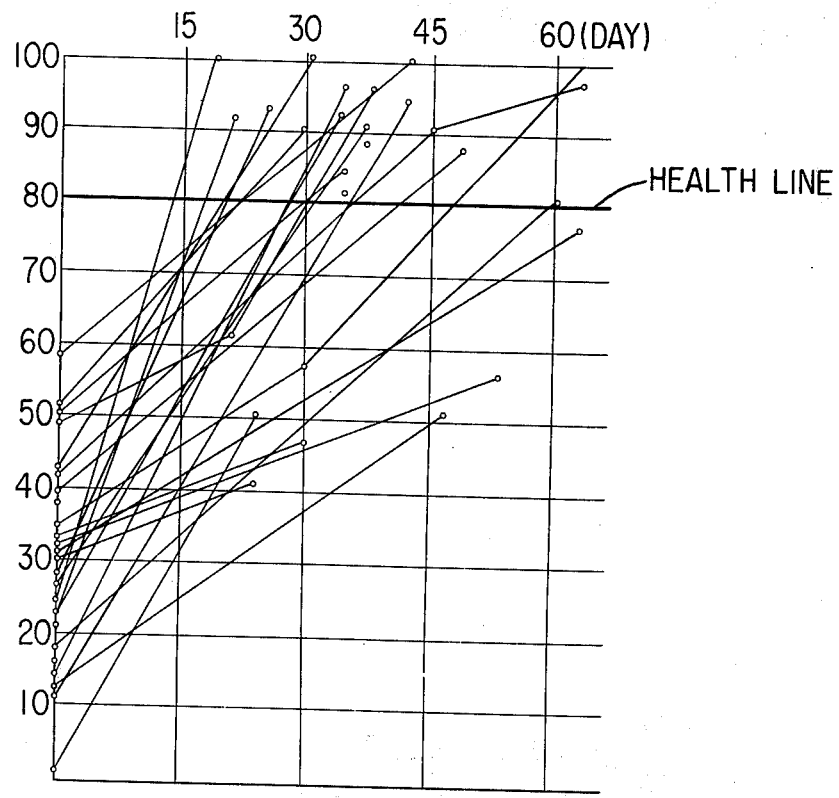

FIG. 6 shows improvement of the stability rate of the autonomic nervous system (measured by neurometer) by the efficacy of the tonic composition. This FIG. 6 includes 25 cases and each case improved its stability to cross over the health line of 80% as time goes by.

Further, when the tonic composition of the present invention is used for 30 – 40 days, about 90% of cases go beyond the health line.

In the use of the tonic composition for animals, it has been experimentally confirmed that the tonic added at a weight ratio of about 1 to 100 of the feed produces the best results. The assortment of effects which the tonic composition of this invention brings about in the systems of domestic animals, e.g. pigs, hens, cattle, trout and eels, and may be summarized as follows: (1) It encourages and promotes enzymatic activities within the various internal organs, (2) provides specific pharmacological functions, (3) provides a specific deodorizing effect, (4) produces no secondary effect in prolonged usage, (5) does no harm to animals, (6) comforts the tips of teats, (7) alleviates skin diseases, (8) assists in easy delivery of offspring, (9) increases the digestive and assimilative ability and consequently decreases the residual protein content in faeces to a great extent, (10) lowers the nitrogen content in the faeces to provide increased fertilizing effect and (11) contributes to the organic stratification of soil. Specifically, in the case of pigs, the tonic provides rapid deodorization of the pigs' bodies and their faeces, promotes their growth, encourages the pigs' liking for feed, heightens the feed efficiency (accelerates the rate of body weight increase), activates and promotes the various functions of the internal organs, promotes the efficiency of disposal of soil and gives many benefits with small expense entailed. In the case of raising chickens for broilers the tonic stops the objectionable odor of the chicken house, encourages the chickens' liking for feed, improves the feed efficiency and activates the functions of the internal organs to provide added resistance to diseases. In the case of raising hens for producing eggs, the tonic improves the quality and the taste of eggs laid and heightens the egg-laying ratio in addition to the effects described above in connection with chicken raising. In the case of raising cattle for dairy products and meat, the tonic improves the quality of milk, the quality of meat and the taste of related products besides the same effects as mentioned above. In the case of raising fish (e.g. eels and trout) the tonic ensures well-balanced fish growth, improves the fishes+ liking for feed, heightens the feed efficiency, and activates the functions of the internal organs and gives added resistance to diseases.

The reaction of the tonic composition upon the living bodies of animals other than man is such as to manifest direct, pronounced effects unlike those produced on the human system. First, the tonic permits the living bodies of animals to acquire surprisingly high resistance to diseases and renders the administration of medicines unnecessary. As to the improvement in business economy, the tonic provides more than 10% by weight savings in feed, and improved the well-balanced growth and body weight increase as well as the quality of meat and eggs, and enhances the taste of products. In the case of the human system, balanced enrichment of the constitution and caloric value of the food ingested are improved by the tonic to give much enhanced vitality as compared with the human system prior to the use of the tonic. Thus, the use of the tonic enriches the physical strength, normalizes the constitution and gradually builds up strong resistance to diseases. The enzymatic activities brought about by the ingestion of the tonic composition of this invention assists in the creation of the cells immunized to diseases.

As described above, the tonic composition according to this invention is effective in promoting the health of the human system. This is because the tonic alkalinizes and consequently cleans the blood. The active component of the tonic composition is contained in the form of acetic acid in a concentration of about 1 to 3% by weight. From the standpoint of chemical reaction, therefore, it naturally produces an acidic reaction. Physiologically, however, it produces an alkaline reaction. It is because of this principal component that the tonic balances the pH status of the body fluid and provides effective recovery from fatigue. Within the systems of animals, the acetic acid has an important part to play, in conjunction with lactic acid and propionic acid, in the formation of milk fats from carbohydrates and fats. Thus, the tonic makes a great contribution to the improvement of the quality of milk, particularly of milk fats.

The invention is further illustrated by the following Examples and tests involving the use of the tonic composition according to this invention.

EXAMPLE 1

In a kiln built of bricks and having an area of about 5.2m × 4.6m and a height of 1m, amorphous carbon and wood vinegar were obtained by carbonizing and roasting, for 240 hours at the temperature range from 300° to 350° C, barks and chips of various trees such as Akagashi (*Quercus acuta* Thunb), Shirogashi (*Quercus myrsinaefolia* Blume), Aragashi (*Quercus glauca* Thunb.), Ichiigashi (*Quercus gilva* Blume), Kojii (*Shiia cuspidata* Makino), Itajii (*Shiia Sieboldii* Makino), Shiratabu (*Litsea glauca* Sieb.), Benitabu (*Machilus Thunbergii* Sieb.), Camphore tree (*Cinnamonum Camphora* Sieb.), Wild cherry tree (*Pronus donarium* Sieb. var. spontanea Makino), Yusu (*Distylum racemosum* Sieb. et Zucc.), Beech (*Quercus serrata* Thunb.), Kunugi (*Quercus acutissimia* Carruth), Japanese Oak (*Fagus crenate* Blume), Hombeam (*Carpinus laxiflora* Blume), Mizume (*Betula grossa*

Sieb. et Zucc.), Maple tree (*Acer plamatum* Thunb.), Zelkova tree (*Zelkova serrata* Makino), Myrica (*Myrica rubra* Sieb. et Zucc.), Scabu (*Euphorbia pekinensis* Rupr. var. japonensis Makino), Harigiri (*Kalopanax septemlobus* Koidz.), Shemp nut (*Pterocarya rhoifolia* Sieb. et Zucc.), Walnut (*Juglans mandshurica* Maxim. var. Sieboldiana Makino), Camellia (*Camellia japonica* L.), Himeshara (*Stewartia monadelpha* Sieb. et Zucc.), Oak (*Quercus dentata* Thunb.), Wax tree (*Rhus succedanea* L.), Japanese cedar (*Cryptomeria japonica* D. Don), Ground-cypress (*Chamaecyparis obtusa* Endl.), Pine tree (*Pinus Thunbergii* Part.), Hemlock spruce (Tsuga Sieboldii Carr.) and White fir (*Abies firma* Sieb. et Zucc). The wood vinegar thus produced was filtered to remove tars and allowed to stand at rest in a storage tank for 5 years. The supernatant layer formed in the wood vinegar after standing was removed and filtered. The filtrate (refined wood vinegar) was added to benzene in a volume ratio of 10 parts of wood vinegar to 2.5 parts of benzene and then agitated. The upper layer of the agitated solution was removed and the bottom layer was transferred into another container. This procedure was carried out 2 or 3 times. The wood vinegar consequently obtained was placed in a container and heated to about 40° C to drive off benzene.

This refined wood vinegar was further distilled to remove about 0.5 - 10% of a fraction having a low boiling point of not more than 100° C at normal pressure and about 10 - 15% of a fraction at not less than 103° C at normal pressure. Thus, about 72% of the refined wood vinegar was obtained. This refined wood vinegar was thus repeatedly distilled until no formaldehyde, 1-3 benzpyrene and others came to be detected. Comfrey leaves were permeated in this refined wood vinegar at a volume ratio of 1 part of comfrey leaves to 100 parts of the refined wood vinegar to disperse the component of the comfrey leaves into the refined wood vinegar. And the resultant refined wood vinegar was filtered to produce the tonic composition for man and other animals.

The tonic composition for man and other animals obtained according to Example 1 has the following main ingredients.

| Mineral ingredients | |
|---|---|
| Potassium | 1.5 ppm |
| Calcium | 1.3 ppm |
| Magnesium | 0.2 ppm |
| Iron | 1.6 ppm |
| Allantoin | 1.31 ppm |
| Pure protein | 0.03 % |
| Vitamin $B_2$ | 0.02 mg% |
| Vitamin $B_{12}$ | 0.2 m$\mu$/ml |
| Germanium | 1.86 ppm |
| Acid degree | 0.86% |
| pH | 3.7 |

The tonic composition according to this invention exhibits a deodorizing effect because the aforementioned weakly acidic components such as cresol and paracresol interact to remove odors. These components, when absorbed within living systems, are converted into weakly acidic components and, in that form, are effective to remove odors. Further, while the organic substances are undergoing fermentation in a digesting tank or cesspool, the enzyme components cause catalytic reactions and diffusing actions to enhance the deodorizing activity. In this case, other components synergistically act with these components to make some contribution to the deodorizing effect.

EXAMPLE 2

The procedure of Example 1 was repeated, except that 97% comfrey leaves, 1% bamboo leaves, 1% garden radish leaves and 1% matrimony vine leaves were used instead of comfrey leaves.

The tonic composition for man and other animals obtained according to Example 2 has the following main ingredients.

| Mineral ingredients | |
|---|---|
| Potassium | 1.0 ppm |
| Calcium | 1.3 ppm |
| Magnesium | 0.1 ppm |
| Manganese | 0.2 ppm |
| Silicone | 2.0 ppm |
| Phosphorus | 2.7 ppm |
| Iron | 1.2 ppm |
| Allantoin | 0.3 ppm |
| Pure protein | 0.01 % |
| Vitamin $B_2$ | 0.1 mg% |
| Vitamin $B_{12}$ | 0.1 m$\mu$/ml |
| Germanium | 0.4 ppm |
| Acid degree | 0.4 % |
| pH | 3.5 |

EXAMPLE 3

The liquid tonic composition obtained in Example 1 was added, in three split fractions, each of about 30% by weight, to a soft amorphous carbon powder of a particle diameter not larger than 300 mesh (ASTM E-11-61) and dried to produce a tonic composition for human use. This soft amorphous carbon powder was obtained by causing the same barks and chips of the trees as used in Example 1 to be carbonized at 350° C for 240 hours in a kiln having an area of about 5.20 m × 4.60 m and a depth of 1 m and finely dividing the resultant carbonization product to a particle diameter finer than 300 mesh (ASTM E-11-61) by means of a pulverizer.

The ingredients of the tonic composition for man and other animals obtained was observed containing 13.5% soft amorphous carbon powder other than those contained in the tonic composition produced according to Example 1.

EXAMPLE 4

The procedure of Example 3 was repeated, except that the soft amorphous carbon powder had a particle diameter in the range of 150 to 200 mesh (ASTM E-11-61). Thus was obtained a tonic composition for animal use.

EXAMPLE 5

Dried comfrey leaves were added to the refined wood vinegar obtained in Example 1 at a ratio of 1 part of comfrey leaves to 100 parts of the aforesaid refined wood vinegar and allowed to stand at rest therein for four months. Thereafter, it was treated by repeating the procedure of Example 1.

Clinical data and tests on the use of the tonic composition according to this invention will be described herein below.

CLINICAL DATA 1:

A male patient 32 years old who vomited and had epigastrum pain and anorexia since the beginning of October, 1974 went to a hospital and was diagonosed as having a gastric ulcer by a Rontgen examination of the stomach.

In this case, the liquid composition of Example 1 was used and he stopped taking other medicaments. The composition of 1.0cc was given to him 3 to 4 times a day. The total amount of the composition given was 3.0 - 4.0cc per day. Said symptoms were comparatively alleviated and the pain disappeared within about 10 days of the first application of the composition. Successively, he took the liquid composition of 1.0 cc 3 times a day. After about one month, the symptoms disappeared, so that when he had a Rontgen examination of the stomach it was diagnosed that the gastric ulcer had almost cured.

CLINICAL DATA 2:

A female patient 40 years old had had lumbago in the balance for a few years. Her symptoms became bad in September, 1974. After a Rontgen examination at a hospital she was diagnosed as having apondyolisthesis. She had received various medical treatments there, but no sign of recovery was seen.

1.0cc of the inventive composition was given her prior to each meal 3 times a day. On the 7th day, lumbago began to be cured little by little. During the above period obstipation was cured. On the 14th day lumbago was almost cured, and she could lead an ordinary life. And anorexia disappeared. When 4 weeks had past, disorders of menstruation became normal, and lumbago and constipation were cured.

CLINICAL DATA 3:

Dr. K, a pediatrician practicing in Kita-ku, Osaka City, was attacked by a sudden appearance of hematuria in January, 1972. Upon examination of his system, the Urological Department of Kyoto University Hospital diagnosed his case to be tuberculosis of both kidneys, with the right kidney completely deprived of its function and the left kidney complicated by renal calculus. In January, 1973, he underwent a surgical operation for extirpation of his kidney. In February of the same year, he underwent another surgical lithotomy for granulation of renal calculus. For a short time that followed, his disease appeared to be alleviated. In September of that year, however, adhesive closure occured in the ureter extending from the remaining left kidney to the bladder. He was immediately sent to the hospital and operated upon for nephrophthisis. Having a catheter inserted through the left abdominal region into the bladder and a urinary bag attached to the external end of said catheter, he was barely saved from the crisis. He was no longer able to rely on the antitubercular agent which he had customarily been taking since the onset of the disease because of side effects of the agent.

In the early part of December of the same year, he was informed of the high efficacy of the product of the present invention and began to take it in the form of internal medicine which was prepared according to Example 1. From the third day, the urine became nearly transparent and he felt energy return spontaneously. On the seventh day, he could go by himself to Kyoto University Hospital. As a result of various examinations, the hospital assured him that the remaining kidney had been incredibly improved in its excretory function.

Dr. K is said to enjoy steady recovery from the disease and consequently started consulting his patients every other day in April, 1973.

CLINICAL DATA 4:

Mrs. S, a 41-year-old housewife and mother of two children, is a sister-in-law of Mr. T, a friend of mine. She lives in the suberb of Osaka City. Four years ago, she suffered from gastritis and gastroptosis and received about a half year's medical treatment. She faithfully dieted on boiled unpolished rice and was completely cured of the disease. Two years ago, she gave up the diet and began to take polished rice and nutritious food in the hope of putting on weight. As a result, she came to enjoy target proportions of 50 Kg of weight to 150 cm of height. In the early part of May 1975, she experienced serious hematemesis all of a sudden and fell unconscious. She was carried by ambulance to a hospital, where the examination showed her blood pressure to have fallen so heavily that with the physical strength remaining in her system, she could not have a surgical operation. Mr. T and his wife came to seek advice on March 6 and told that she was barely surviving due solely to blood transfusions.

Mrs. T flew to Osaka, taking two week's doses of the aqueous product of Example 2 and the powder product of Example 3. She cared for the patient, making a cream of boiled unpolished rice and encouraging the patient to take it. Mrs. T is quoted as admitting that her purpose of the visit was to persuade the patient and her husband into refusing to receive a surgical operation even if she regained her physical strength sufficiently.

Several days later, Mrs. T was informed that her sister had regained physical strength sufficiently that the scheduled surgical operation would be performed on the evening of March 12. Mrs. T once again went to Osaka and asked the physician in charge to postpone the operation by one month. After the patient had completed the second 2 week's doses of the medicine, her gastric system was given an elaborate examination by means of X-ray equipment and a gastric camera. The examination failed to detect any trace of ulcer. The physician is said to admit that he has never experienced such a miraculous efficacy of a medicine.

Admittedly there are cases in which the X-ray examination fails to detect any hemorrhagic region in stomaches which have experienced ulcerous hemorrhage. In any event, the present case ought to be regarded as that of an exceptional success in consideration of the fact that an abdominal operation was obviated.

Test 1: Use of the tonic in chicken-raising 150 young hens raised for egg-laying for 60 days after their birth, were given a feed containing the tonic composition of Example 1 (liquid) in an amount of 1 cc per day per hen for 150 days. The hens started laying eggs 25 days, on the average, earlier than other hens which were given a feed not containing the tonic composition of this invention. None of the hens suffered from disease and the odor of the faeces was reduced to a remarkable extent.

Test 2

The tonic composition (liquid) produced by the method of Example 2 was given to one group of chickens for broilers and not given to another group for comparison of growth ratio, weight increase ratio, feed efficiency, limb meat yield and regular meat yield. The results as shown in Tables 5 and 6 indicate the following facts.

1. Growth ratio: For the first 56 days, the growth ratio was 100% for both the groups, with no difference. The growth ratio for the first 70 days was 100% for the test group and 98.6% for the control group respectively in the case of the chickens of Group A. In the case of the Group B, the growth ratio was 100% for both groups.

$$\text{Growth ratio (\%)} = \frac{\text{No. of birds which underwent test}}{\text{No. of birds to which feeding was started}} \times 100$$

2. Weight increase ratio: Weight increase ratios during the ages of 11 days and 56 days and between those of 56 days and 70 days were as shown in the table.
3. Feed efficiency: The feed efficiency was 0.1 lower for the test group than for the control group.

$$\text{Feed efficiency} = \frac{\text{Feed consumption per month (g)}}{\text{Weight of eggs laid per month (g)}}$$

4. Lamb meat yield: No discernible difference was observed between the two groups. For the comparison, limb meat was taken from all chickens of each group.
5, Regular meat yield: For comparison, the meat taken from 5 chickens of each sex. The regular meat was taken from 2 chickens of each sex.

| Test group | 124 (with agent added) | 11 to 30 days of age – 0.2 ml<br>31 to 70 days of age – 0.4 ml |
|---|---|---|
| Control group | 124 (no agent added) | |
| Management of raising | The chickens were all raised in a windowed chicken house with a ground-level floor. | |
| Feed | –Between ages of 0 and 28 days – commercially available feed formulated for young broilers, 23 – 76.<br>Between ages of 28 and 70 days – commercially available feed formulated for broilers of advanced growth stage, 20 – 80. | |

Test 3 (Use of tonic in pig raising)

For 100 days, 48 pigs having an average weight of 40 kg were fed on a feed prepared by adding to leftovers the tonic composition (liquid) of Example 1 in an amount corresponding to 1% based on said leftovers. Compared with a group of pigs fed on the same leftovers omitting the addition of the tonic composition, the pigs of the test group showed healthful growth, accelerated body weight increase by an average of 15%, complete freedom from disease, improved quality of meat (thin fat layers), decreased body odor and sharply reduced faecal odor.

An anatomical observation performed on the pigs failed to detect occurences of round-worms within the intestinal interior. The intestines from the pigs of the test group were found to be very resilient.

Table 5

| Classification | | | Test group | | | | Control group | | | |
|---|---|---|---|---|---|---|---|---|---|---|
| Species | | | Group A | | Group B | | Group A | | Group B | |
| Sex | | | ♂ | ♀ | ♂ | ♀ | ♂ | ♀ | ♂ | ♀ |
| Number of birds to which feeding was started | | | 31 | 39 | 28 | 26 | 34 | 36 | 28 | 26 |
| Number of birds which underwent test | | | 31 | 39 | 28 | 26 | 33 | 36 | 28 | 26 |
| Growth ratio % | | | 100 | | 100 | | 98.6 | | 100 | |
| Average weight (Kg) and standard deviation | 70 days of age | Average X | 2.48 | | 2.49 | | 2.34 | | 2.48 | |
| | | | 2.818 | 2.140 | 2.830 | 2.148 | 2.663 | 2.012 | 2.789 | 2.163 |
| | | S D | .163 | .124 | .212 | .215 | .238 | .142 | .235 | .178 |
| | 56 days of age | | 2.24 | | | | 2.34 | | | |
| Feed efficiency | 70 days of age | | 2.57 | | | | 2.67 | | | |
| Limb meat yield, % | | | 75.4 | | 75.2 | | 74.4 | | 75.3 | |
| Regular mat yield, % | | | 30.3 | | 32.0 | | 39.4 | | 30.0 | |

Table 6

| | | Weight increase (average/bird, in g) | | |
|---|---|---|---|---|
| Group | Period | Ages of 11 – 56 days | Ages of 11 – 70 days | Ages of 56 – 70 days |
| A ♂ | Test group | 1.888 | 2.653 | 765 |
| | Control group | 1.791 | 2.493 | 702 |
| | Index | (105) | (106) | (109) |
| A ♀ | Test group | 1.454 | 1.985 | 531 |
| | Control group | 1.397 | 1.856 | 459 |
| | Index | (104) | (107) | (116) |
| B ♂ | Test group | 1.867 | 2.662 | 795 |
| | Control group | 1.908 | 2.623 | 715 |
| | Index | (98) | (101) | (111) |
| B ♀ | Test group | .1.478 | 1.988 | 510 |
| | Control group | 1.512 | 2.006 | 494 |
| | Index | (98) | (99) | (103) |

Remarks: The indexes given in parentheses indicated weight increasess for given test groups calculated by assuming weight increases for corresponding control groups as 100 respectively.
Materials and method:
Chickens used in test - A total of 248 chicks (for broilers) hatched on 18 July 1971
Test period - 70 days following start of feeding
Test grouping  Number of birds to  Daily dose in water
               which feeding was    (per bird/day)
               started Test 4:

The tonic composition (liquid) prepared according to Example 2 was used in pig raising to determine what effect the addition thereof would bring about in removing objectional odor and in improving the efficiency of pig raising. The results of the comparative study are shown in the following Table 7.

Table 7

| Grouping | Control group | | | | Test group | | | |
|---|---|---|---|---|---|---|---|---|
| | Date | Number of pigs | Weight | Remarks | Date | Number of pigs | Weight | Remarks |
| Young pigs purchased | Jul. 26, 1970 | 9 | | | Jul. 26, 1970 | 9 | | |
| Test started | Aug. 1, 1970 | 9 | 401.9 | | Aug. 1, 1970 | 9 | 385.3 | |
| Average body weight | Aug. 1, 1970 | | 44.6 | | Aug. 1, 1970 | | 42.8 | Though a symptom resembling SEP appeared, it showed little sign of progress and was cured without use of any medicine. |
| Contraction of disease | Aug. 22, 1970 | 1 | | Medicine for SEP given | | | | |
| Fatality | Aug. 29, 1970 | 1 | 48.0 | | | | | |
| Contraction of disease | Aug. 22, 1970 | 1 | | Medicine for SEP given | | | | |
| Shipment of ill pig | Oct. 13, 1970 | (1) | (52.0) | | | | | |
| Contraction of disease | Sep. 20 1970 | 1 | | Medicine for toxo. given | | | | |
| Fatality | Sep. 22, 1970 | 1 | 66 | | | | | |
| Feed | | | 2435.0 | | | | 2635.0 | |
| Feed efficiency | | | 3.3 | | | | 3.1 | |
| Shipment | Oct. 13, 1970 | | | One ill pig, 52 K included | | | | |
| | Nov. 4, 1970 | | | Two pigs, 108 K met death | Nov. 4, 1970 | | 851.5 | No pigs dead |
| | Nov. 23, 1970 | 7 | 728.5 | | | | | |
| Objectional odor | | | | Objectionable odor persisted | | | | Very little odor remained. Body odor hardly perceivable. |

Note:
The tonic composition was added in an amount corresponding to 1/100 of the feed.
"Sep" stands for swine enzootic pneumonia.
"toxo" stands for toxoplasmosis.
Used medicines are Aurofac, Tephpare and Tyrocine.

From the preceding results, the following facts have been brought to light.

1. The objectional odor was nearly completely absent. The pigs' bodies hardly smelled offensive. The objectionable odor began to decline about one week after start of the use of the tonic.

2. As regards the efficiency of growth, when pigs were divided into the control group and the test group at the start, there was difference of about 1.8 kg of average weight. Apparently, the pigs of the control group were quite healthy and at first showed more appetite for the feed than those of the test group.

3. Among the pigs of the test group, a symptom resembling SEP was observed in one pig. The pig, with no medicine administered, was placed under careful observation. The disease developed very little. The pig recovered health in 3 days.

4. No medicine of any sort was administered to the pigs of the test group.

5. In the control group of pigs which at first enjoyed healthful growth, 3 pigs contracted diseases (2 pigs died and one pig was shipped out to the meat market).

6. A larger weight increase was shown despite a smaller feed requirement (less by 0.2 kg).

7. Absence of contraction of disease indicates that the pigs acquired increased resistance to disease.

8. The fixed consumption of the tonic at the pig farm (capacity for 420 pigs) was roughly 340 liters (kg) (17 cases) (bags).

9. The results indicate that consumption of the agent is enough to ensure ideal pig growth and thorough elimination of the objectional odor.

Test 5

The tonic consumption (liquid) according to Example 1 was used in raising pigs (Berkshire). A feed having the tonic incorporated by an amount of 1/100 of the amount of feed and a feed omitting the addition of the tonic were tested to determine what effect the use of the tonic would bring about in improving the growth efficiency and the removal of offensive odor. The results of the comparison are shown in the following Table 8.

Table 8

| Group | Division | Feed efficiency (20 – 90 kg) | Average daily weight increase | Weight at time of slaughter | Number of round worms within intestines |
|---|---|---|---|---|---|
| Group A | Control | 3.50 | 559 | 79 kg | 2 |
| | Test | 3.45 | 566 | 82 | 1 |
| Group B | Control | 3.28 | 617 | 84 | 6 |
| | Test | 3.17 | 636 | 87 | 0 |

(Note)
Species of pigs used in test - Berkshire
Amount of tonic used - 1/100 of feed
Period of test - four months Growth efficiency (test group with feed incorporating tonic - improved and accelerated growth).

1. Feed incorporating the tonic encouraged the pigs' liking for the feed, with their appetite particularly heightened during the body weight stage of 50 to 90kg.
2. The feed requirement was smaller for the test group (using the feed incorporating the tonic) than for the control group. Nevertheless, the average daily weight increase was greater for the test group than for the control group.
3. The weight at the time of slaughter was greater for the test group than for the control group. Deodorizing effect — This effect was conspicuous.
   1. Offensive excrement and body odor were hardly perceivable.
   2. During dissection, no offensive odor emanated from the interior of the intestines.

Occurrence of round-worms at the time of dissection;

In the pigs of the control group, an average of 8 round-worms was observed in the intestines. In those of the test group, the average was 1 round-worm.

Test 6

When the tonic consumption (powder) according to Example 4 was used on hens raised in a chicken farm (egg-laying), it served to remove the offensive odor of hens' droppings improve the egg quality and heighten the survival ratio and feed efficiency. The results are compared in the following tables 9 and 10 with the results obtained for the control group.

Table 9

| Group | Number of hens used in test | Ratio of addition | Remarks |
|---|---|---|---|
| Control | 99 | 0 | |
| Test | 100 | 1% | Test for one month |

(Note) Species of hen - Decarb 371

Table 10

| Item | | Test group | Control group | Remark |
|---|---|---|---|---|
| Number of hens | | 100 | 99 | |
| Survival ratio | | 99 % | 100 % | One hen died of intestinal inflammation |
| Total hen days | | 2,999 | 2,970 | |
| Number of eggs laid | | 2,230 | 2,176 | |
| Egg weight | | 121,360 g | 116,790 g | |
| Average egg weight | | 54.4 g | 53.7 g | |
| Egg-laying ratio | | 74.4 % | 73.3 % | |
| Average egg yield | | 40.5 g | 39.3 g | |
| Feed consumption | | 291,900 g | 341,100 g | |
| Average daily feed consumption | | 97.3 g | 114.8 g | |
| Feed efficiency | | 2.41 | 2.92 | |
| Thickness | Dull end | 0.401 | 0.361 | |
| of egg | Equinox | 0.374 | 0.353 | |
| shell | Sharp end | 0.414 | 0.381 | |

The preceding test data indicate the following facts:
1. Survival ratio — No significant difference was observed between the test group and the control group.
2. Egg-laying ratio — the egg-laying ratio was 1.1% higher for the test group than for the control group.
3. Average egg weight — The average egg weight was 0.7 g heavier for the test group than for the control group.
4. Average daily egg yield per hen — The test group showed an increase of 1.2 g of yield over that of the control group.
5. Average feed consumption per hen per day — The control group consumed 17.5 g more than the test group.
6. Feed efficiency — The test group showed an efficiency 0.51 higher than that of the control group.
7. Test of egg quality
   a. The Haugh unit was height of egg content after breaking shell-better in the test group than in the control group.
   b. The shell thickness was greater for the test group than for the control group. The shell thickness was particularly large at the sharp end, followed by the dull end and the equinox.
8. Economy — The profit was ¥18 per hen greater for the test group than for the control group.
9. Condition of offensive odor — The usual odor on a chicken farm persisted in the control group, while practically no odor was perceivable in the test group.

Through the tests described above, it has been ascertained that the addition of the tonic composition according to this invention, when given to domestic animals, encourages the animals' liking for their feed, promotes the health and growth of animals, prevents diseases, deodorizes their faeces and bodies, and serves effectively in improving the hygienic condition of their environment. The tonic composition prepared in the form of a granular or powdery solid adsorbed on a soft amorphous carbon powder is as effective as the liquid tonic described above. Moreover, the soft amorphous carbon powder, when introduced into the internal systems of the animals, serves to adsorb gases of indole and skatole type occurring as a consequence of the hydrolysis of starch present in the animals' feed and at the same time functions to control the environment of microorganisms within their systems.

What is claimed is:

1. A method for manufacturing a composition, comprising:
   a. preparing wood vinegar by heating and cooling chips of wood and bark and then allowing said wood vinegar to stand at rest and separate into two layers, removing the supernatant layer, washing the supernatant with benzene and then distilling the washed supernatant thereby obtaining refined wood vinegar free of soluble tars unsuitable for ingestion by man or other animals;
   b. immersing in said refined wood vinegar leaves of plants in an amount in the range of about 0.1 to 10 parts by weight per 100 parts of said refined wood vinegar, said leaves comprising:
      85 — 100% by weight comfrey leaves
      0 — 15% by weight bamboo leaves
      0 — 15% by weight garden radish leaves
      0 — 15% by weight matrimony vine leaves
   c. allowing said leaves to be permeated and fermented by said refined wood vinegar causing extracts from said leaves to be removed by said refined wood vinegar, and d. filtering the refined wood vinegar containing said extracts thereby removing solid remains of said leaves and obtaining a composition.

2. A method according to claim 1 wherein said chips of wood and bark are selected from the group consisting of deciduous tree wood and a mixture containing a major fraction of deciduous tree wood and a minor fraction of coniferous tree wood.

3. A method according to claim 2 wherein said mixture contains 90 — 99% by weight of deciduous tree wood and 10 – 1% by weight of coniferous tree wood.

4. A composition manufactured by the method of claim 1.

5. A method according to claim 1 wherein said composition is adsorbed on soft amorphous carbon powder and zeonerite.

6. A method according to claim 5 wherein said soft amorphous carbon powder is obtained by roasting wood selected from the group consisting of deciduous tree wood and a mixture containing a major fraction of deciduous tree wood and a minor fraction of coniferous tree wood.

7. A method according to claim 6 wherein mixture contains 90 — 99% by weight of deciduous tree wood and 10 — 1% by weight of coniferous tree wood.

8. A granular or powdery composition manufactured by the method of claim 5.

9. A method according to claim 1, wherein said wood vinegar is allowed to stand at rest for several years.

10. A method according to claim 9, wherein said wood vinegar is allowed to stand at rest for more than five years.

11. A method according to claim 1, wherein any soluble tars remaining after the washing with benzene and distilling steps, are removed by repeated distillation, agitation and standing.

12. A method according to claim 1, wherein the comfrey leaves comprise at least 90% by weight of said leaves.

13. A method according to claim 6, wherein said roasting is conducted at about 250° to 450° for about 20 to 500 hours.

14. A method according to claim 13, wherein said roasting is conducted at about 350° C.

15. A method according to claim 13, wherein said roasting is conducted for about 200 to 300 hours.

16. A composition manufactured by the method of claim 2,

17. A composition manufactured by the method of claim 3.

18. A composition manufactured by the method of claim 9.

19. A medicinal composition for human beings comprising about 3 to 4cc of the composition of claim 4 distributed with 50 to 100 times, by volume, of water.

20. A medicinal composition for human beings comprising about 3 to 4cc of the composition of claim 16 distributed with 50 to 100 times, by volume, of water.

21. A medicinal composition for human beings comprising about 3 to 4cc of the composition of claim 17 distributed with 50 to 100 times, by volume, of water.

22. A medicinal composition for human beings comprising about 3 to 4cc of the composition of claim 18 distributed with 50 to 100 times, by volume, of water.

23. A granular or powdery composition manufactured by the method of claim 6.

24. A granular or powdery composition manufactured by the method of claim 13.

25. A granular or powdery composition manufactured by the method of claim 14.

26. A granular or powdery composition manufactured by the method of claim 15.

* * * * *